United States Patent [19]

Pinto

[11] Patent Number: 4,657,761

[45] Date of Patent: Apr. 14, 1987

[54] POLYVALENT NON-SPECIFIC IMMUNO-STIMULATING VACCINE AND METHOD

[76] Inventor: Cesar M. Pinto, 10 Calle 3-01 Zona 14, Guatemala C, Guatemala

[21] Appl. No.: 741,344

[22] Filed: Jun. 5, 1985

[51] Int. Cl.$^4$ .............................................. A61K 39/00
[52] U.S. Cl. ........................................ 424/88; 424/85; 424/89; 424/92; 514/825; 514/859; 514/863; 514/894; 514/903; 514/931; 514/934; 514/885; 514/896
[58] Field of Search ............................ 424/88, 89, 92; 514/825, 859, 863, 894, 903, 931, 934, 885, 896

[56] References Cited

U.S. PATENT DOCUMENTS

| | | | |
|---|---|---|---|
| 206,940 | 11/1923 | Redlie | 424/92 |
| 4,341,762 | 7/1982 | Haast | 424/88 |
| 4,351,827 | 9/1982 | Biylenga | 424/89 |
| 4,584,194 | 4/1986 | Bass | 424/89 |

FOREIGN PATENT DOCUMENTS

| | | | |
|---|---|---|---|
| 0141416 | 11/1980 | Japan | 424/92 |
| 1270918 | 4/1972 | United Kingdom | 424/89 |

OTHER PUBLICATIONS

Meyer et al, "Combined Measles Small Pox and Other Vaccines", *Vaccine Against Viral... Man*, by U.S. Dept. Health, Education and Welfare, 1967, pp. 336–342.
Landi et al, "Highly Specific Tuberculin", *C.A.*, vol. 87, 1977, #132212b.
"Stablization of Mumps Vaccine", *C.A.*, vol. 96, #187300v.

*Primary Examiner*—Morton Foelak
*Assistant Examiner*—Garnette D. Draper
*Attorney, Agent, or Firm*—Irvine A. Lavine

[57] ABSTRACT

A non-specific therapeutic polyvalent vaccine for subcutaneous injection containing a minimum combination of a PPD (tuberculin vaccine), a rabies vaccine, and snake venom vaccine and preferably including at least a DTP vaccine in addition and optimally a mumps antigen vaccine and Dermatophytin vaccine in controlled levels, all such constituent vaccines being commercially available. The vaccine provides a broad-based stimulation or potentiation of the immuno-defense system of the patient and is useful for the symptomatic relief and/or mitigation of diseases of viral origin, such as Herpes Zoster, labialis and genitalis, various neuralgias, mumps, measles, viral hepatitis, psoriasis and severe acne, or of autoimmune origin, such as multiple sclerosis and arthritis.

8 Claims, No Drawings

POLYVALENT NON-SPECIFIC IMMUNO-STIMULATING VACCINE AND METHOD

FIELD OF THE INVENTION

This invention relates to a polyvalent vaccine composition and is concerned more particularly with a vaccine composition containing a plurality of distinct antigenic components, selected in specified combinations from certain well known therapeutic vaccines, for purposes of evoking in a patient receiving the same a non-specific stimulation or potentiation of the natural immunodefense system of the patient for achieving significantly symptomatic relief or mitigation of a number of diseases, particularly of viral, bacterial, fungal and autoimmune origin.

BACKGROUND OF THE INVENTION AND PRIOR ART

When a protein is introduced into the blood stream of an animal, including humans, to which that protein is foreign, the protein acts as an antigen and elicits an immunological response which results in a cell mediated response and in the production of antibodies of the immune system of the animal. Such antibodies are specific to the particular injected antigen in the sense that a given antibody will bind in a complex as an immune reaction, i.e., undergo complexation, only with the specific antigen by which it was generated but may also produce cross-reactions between an antibody and antigens closely related to that for which such antibody is specific.

When an animal is invaded by a disease-producing organism which enters its system, the invading organism acts as an antigen and thus eventually evokes an immune response thereto. However, if the animal has never previously been exposed to the particular invading organism, its system has had no opportunity to produce antibodies to that organism so that the immunological response of the animal may be slow to develop and before such development has taken place, the attack of the organism may have become so invasive or massive as to cause a prolonged illness or even death if the animal's immunological defenses are sufficiently overwhelmed.

In order to convey an immunity in advance to the attack of serious disease-producing organisms, vaccines have been developed which are traditionally administered for prophylatic purposes, i.e., to expose the animal to a specific invading disease-producing antigen in such limited quantities or in such an inactivated or weakened condition that the immunological system of the body can safely develop an adequate supply of antibodies for the pathological antigen as to confer protection against subsequent exposures to that antigen but without seriously risking an invasive attack by the administered antigen, although unfortunately such attacks can occur in rare instances with, for example, hypersensitive individuals.

Obviously, since the prophylactic approach can rarely be totally implemented throughout an entire population, it is desirable to have available to the physician therapeutic resources that can be administered to patients already suffering with a given disease. The fact that the disease is already in progress in a patient naturally denotes that the immunological defenses of that patient were insufficient to withstand the invasion of the disease, and reinforcement or stimulation of the thus inadequate immunological defenses can be achieved in two ways. First, a serum or antitoxin can be derived from the blood of another individual who was previously exposed to the particular disease, either naturally or by prophylactic vaccination, and which serum, therefore, already contains antibodies against the specific disease. Various serums have been developed and can be administered to patients suffering from the disease for treatment of same, the antibodies provided by the serum aiding in neutralizing the noxious antigen until the time the patient's own immunological system has become enhanced and is capable of combatting the disease.

Alternatively, in certain instances, therapeutic vaccines have been developed which contain the specific antigen corresponding to the on-going disease to be treated for purposes of therapeutic administration to evoke a stronger immunological reaction for assisting in overcoming the further course of the disease. Generally, such a therapeutic antigenic vaccine is useful for diseases which have an extended incubation period, i.e., a considerable time lapse between time of exposure and actual symptomatic manifestation of the disease in the patient, such as rabies. Obviously, if the disease is already well established, then the introduction of added antigens of the same type is normally contraindicated, serving only to aggravate the existing imbalance between the invading organisms and the already strained immunological defenses of the patient. However, if the onset of the disease is delayed following a recognized exposure, then injection of the same antigen in altered, e.g., weakened form, can serve in the interim to provoke the immunological system to produce antibodies thereagainst which will then be present to combat the development of the disease at the end of its incubation period.

Antigenic vaccines are also administered for diagnostic purposes, i.e., to provide a perceptible indication of whether or not a given individual has been previously exposed to a disease-producing organism and thus already contains antibodies for that organism in its system. An example is the tuberculin vaccine employed to signify the presence or not of antibodies for the tuberculin bacillus.

Typically, where therapeutic antigenic vaccines have been employed, such employment has been specific to the precise antigenic disease-producing organism that is to be combatted or detected as the case may be. Given the known specificity of the antigen-antibody response, it follows that the same antigen needs to be selected for therapeutic intervention for the corresponding disease. For example, if introduction of say a tetanus bacteria into the system is suspected, the physician administers a tetanus vaccine and not a rabies vaccine or a tuberculin vaccine. However, in recent years a non-specific response to antigenic administration has received limited recognition. Thus, it has been proposed to administer a bacille Calmette Guerin (BCG) (see Barber, "Immunobiology for the Clinician", J. Wiley & Sons, 1977, pp. 239, 240) vaccine for the treatment of malignant tumors, particularly in combination with other anti-tumor therapy with some success. BCG has also been proposed in U.S. Pat. No. 3,849,551 as an adjuvant in a non-living malaria vaccine. Such "adjuvants" are considered to lack immunological activity in themselves, but to enhance or promote the immunological response elicited from certain other antigenic materials. Other examples of adjuvants are the so-called Freunds adjuvant, complete and incomplete, which consists of a water-in-oil emulsion containing a suspension of killed tubercle bacilli, as well as mycobacteria other than BCG as disclosed in U.S Pat. No. 3,876,779.

A polyvalent vaccine described as having the capacity to stimulate non-specifically the immune systems of a patient to which it is administered is described in U.S. Pat. No. 4,341,762 to Haast. This vaccine is constituted of a mixture of plural snake venom components: a first component acting as a post-synaptic neurotoxin, derived from "cobra" venom, a second component having a pre-synaptic neurotoxin activity derived from "krait" venom and a third component derived from "viper" venom to which is primarily attributed immuno-stimulating capability, although the other two components are also said to have some immuno-stimulatory effect. This vaccine is said to be useful for the treatment of progressive degenerative neurological diseases such as multiple sclerosis, muscular distrophy and Parkinson's disease, and diseases of known or potential viral origin, such as the herpes complex, and for mitigating autoimmune disorders, such as the arthritis complex, as well as diabetes. The venom components of the Haast vaccine, while not subjected to a chemical detoxification treatment, as characterized an earlier vaccine for neurological disorders described in U.S. Pat. Nos. 3,888,977 and 4,126,676 to Sanders, were rendered safe for human administration by means of individual complex purification and extractive procedures to remove noxious or toxic constituents therefrom, while preserving the bioactivity of the desirable active fractions thereof.

SUMMARY OF THE INVENTION

The present invention is a non-specific therapeutic polyvalent vaccine designed to be injected for the evocation of a multi-antibody response and is, therefore, distinct from a serum or antitoxin. The instant vaccine consists essentially of a specific combination of at least three and preferably up to six separate constituents which are in themselves commonly available vaccine compositions. The invention is predicated on the recognition of the possibility, particularly where the natural immuno-defense system of the patient is in a weakened or debilitated state as is true for various chronic diseases, particularly of the types to be hereinafter identified, that if a combination of radically diverse antigenic agents is administered to the patient in controlled quantities, the immunological system of the patient may be sufficiently stimulated as to function in the generation of cell mediated and humoral immune mechanisms as to function in the development of immune cells and generation of the antibodies in order to exert a resistance to the further course of the disease even where the antigenic nature of the disease in question is unrelated to the antigenic nature of the respective vaccine components.

More specifically, each constituent vaccine carries at least one and more usually a plurality of antigenic determinants thereon, each of which is effective to produce an antibody specific thereto upon injection into the humoral system of the patient. By combining multiple vaccine components, and particularly those carrying multiple determinants, the immunological system of the patient is provoked into the generation of diverse antibodies and other disease-combatting factors such as an interferon, T-cell lymphocytes, etc., which, quite surprisingly in the perspective of conventional immunobiological thought, have been effective to achieve troublesome diseases which up to now have had little or no effective treatment available. It would be appreciated that this is a highly simplified explanation of a possible operative mechanism of the present invention and may overlook important contributions of other factors, bearing in mind that the behavior of the animal immunobiological system and the conceivable consequences thereon of highly active agents as contemplated herein are extraordinarily complicated and only imperfectly understood at the present time.

DETAILED DESCRIPTION OF THE INVENTION

The present invention is a mixture of certain selected commercially available constituent vaccines that are in common use for their own specific therapeutic purposes, and the following is a tabulation of the innoculation levels at which the respective vaccines are typically applied for their regular intended use.

| Typical Innoculation Dose for Following Vaccine to Apply 0.1 ml. s.c. | |
|---|---|
| PPD (Tuberculin) Vaccine | 0.005 ml |
| Rabies Vaccine | 0.01 ml |
| DiTePer Vaccine | 0.005 ml |
| Mumps Antigen Vaccine | 0.005 ml |
| Dermatophytin "O" Vaccine* | 0.005 ml |
| "Proven" Snake Venom Vaccine | 0.07 ml |
| | 0.10 ml |

*Dermatophytin "O" at 1:100 dilution

In the invention the above known constituent vaccines are combined in selected combinations at controlled dosage levels so as to produce the composite polyvalent vaccine of the invention. In its simplest form, the present vaccine is based on the combination of a highly active antigenic vaccine PPD plus a rabies vaccine and a snake venom vaccine. The minimum, normal and maximum amounts for a "nominal" dose of these three components to give a trivalent vaccine that is adequate and effective to achieve a significant potentiation or stimulation of the immuno defense system of the patient with a minimum of unpleasant side effects or discomfort to the patient and without real fear of deleterious or toxic effects.

| | Nominal Dosage Levels of Basic "Trivalent" Vaccine Combination of the Invention (ml) | | |
|---|---|---|---|
| Agent | Minimum | Normal | Maximum |
| PPD Vaccine | 0.001 | 0.005 | 0.01 |
| Rabies Vaccine | 0.005 | 0.01 | 0.10 |
| Snake Venom Vaccine | 0.05 | 0.07–0.1 | 0.15 |

More preferably, this basic combination is further enhanced in its desired effect by the addition of at least the first and preferably all three of the powerfully active antigenic vaccines DPT, mumps vaccine and Dermatophytin vaccine. The corresponding "nominal" dosage levels for the optimum vaccine combination inclusive of these additional strongly antigenic components follows:

| Concentration "Nominal" Dosage Levels for Optimum "Hexavalent" Vaccine Combination (ml) | | | |
| --- | --- | --- | --- |
| Agent | Minimum | Normal | Maximum |
| PPD Vaccine | 0.001 | 0.005 | 0.01 |
| Rabines Vaccine | 0.005 | 0.01 | 0.10 |
| Snake Venom Vaccine | 0.05 | 0.07-0.1 | 0.15 |
| DPT Vaccine | 0.001 | 0.005 | 0.01 |
| Mumps Vaccine | 0.001 | 0.005 | 0.01 |
| Dermatophytin Vaccine* | 0.001 | 0.005 | 0.01 |

*at 1:100 dilution

The four highly antigenic constituent vaccines, i.e., the PPD, DPT, mumps and Ermatophytin vaccines, are as the above ranges indicate allowed to be present in very small closely controlled levels due to their powerful antigenic action and in order to avoid significantly undesirable side effects for the patient, these limits should be closely observed. For example, injection or a composite vaccine containing an excess of PPD above the above specified maximum introduces some risk of a significant necrosis at the side of the injection which while certainly not fatal is not beneficial to the patient and tends to unnecessarily complicate the therapeutic process. Similarly, an excess of DPT can produce convulsions in children. For the other two components; namely, the snake venom vaccine and the rabies vaccine, the antigenic activity levels thereof are considerably weaker and, therefore, the above indicated "maximum" limits are based on amounts which can be easily and comfortably tolerated by the patient and do not represent actual operative ceilings demanding scrupulous observance. Hence, these maximum levels can under appropriate circumstances where additional enhancement of the overall antigenic effect is indicated, be exceeded with little or no deleterious consequences for the patient. The content of the rabies vaccine, in particular, being susceptible to an increase up to 0.2 ml of even 0.5 ml with little or no fear of impermissible ill effects apart from a possible more severe local inflammation at the injection site. On the other hand, where plural powerfully active antigenic components are present, some discretion should be exercised in the adjustment of the operative levels of those components toward the maximum amounts specified above within the clinical experience of the practitioner. That is to say, if an increase in patient response is desired for particular treatment circumstances, then only one or perhaps two of these highly active materials should be considered for such an increase, while any others of this group should be held at lower levels and possibly even reduced below their normal operative levels so as to minimize the opportunity for deleterious effects to the patient. Otherwise and as a general rule, the above concentration levels from minimum to maximum should be applied depending on the required reaction response and state of the patient. In complete anergy the patient may not react even to higher doses.

The above concentration levels are specified in terms of what is nominally acceptable for single innoculation dosages without any intention to necessarily imply that actual working dosages would be prepared individually to conform directly to these constraints, and it would be obviously difficult to load such minute amounts directly into a hypodermic needle. In actual practice, rather, the vaccine components will be combined in much greater quantities in the same proportions corresponding to those given in the above "nominal" tabulations. Then the actual individual dosage amounts would be extracted from this mixture on a dose-by-dose basis. Although a preferred and typical amount for an actual working dose is 0.1 ml of the preferred composite polyvalent formulation set forth above, this working dosage level can be adjusted within reasonable limits according to the experience of the practitioner and the symptomatic condition and prognosis of the individual patient to be treated.

It should be noted that in actual practice, the individual dose of any of the above vaccines used isolatedly for its normal and intended purpose, e.g., a rabies vaccine used to prevent rabies, is many times higher that the doses used in the present composite vaccine. For persons of lesser body weight or whose condition is of mild or less serious nature, or children, the practical dosage level might be cut in half, while for persons requiring a more powerful stimulation of the immuno system, i.e., those in a more serious condition, e.g., in an anergic state, this working dosage can be increased, i.e., doubled, tripled or in extreme cases even more. In general, the present vaccine should not be administered to very young children, say up to one year's age, who are prone to react convulsively.

In addition, while the carefully controlled limits proscribed for the constituent vaccine have been carefully worked out with a view to minimizing the risk to the patient, the administering physician should exercise the usual precautions with the present vaccine as for the injection of any foreign proteinaceous matter into a patient. Certain individuals can exhibit an acute hypersensitivity to even very small amounts of foreign protein matter resulting in anaphylactic shock or other life threatening reaction as can be observed with any biologic product, and while no instance of such adverse reactions has been observed in the extensive testing with several thousand doses of the present polyvalent combination on human patients up to now, the physician should nevertheless be prepared in all instances to apply the usual recognized therapeutic measures against acute hypersensitive manifestations including the injection of adrenalin, steroids, and/or the administration of antihistamines promptly in the event of an acute reaction.

Generally speaking, apart from vaccines serving a diagnostic function where a localized dermal reaction is indispensable to a diagnostic determination, development by the patient of a localized reaction from a vaccine injection due to so-called delayed hypersensitivity is ordinarily deemed to be contraindicated and to be avoided if possible. In contrast to this prejudice against a delayed hypersensitive reaction, the present invention aims at the administration of a sufficient quantity of the composite vaccine as to induce deliberately a perceptible delayed hypersensitive reaction in the patient which is taken as a manifestation of the evocation in the immuno system of the patient of an immune response signifying a stimulation or potentiation of his immuno defense system. Therefore, the ultimate determining factor in adjusting the amount of the dosage to be applied to a specific patient is that amount which will produce at least a light delayed hypersensitive reaction at the injection site.

As is known medically, a delayed hypersensitive reaction is characterized by significant inflammation with redness and induration and edema of the tissue surrounding the locus of vaccination which develops over an extended period of time of at least 8–24 hours following injection and even longer up to 36 or 72 hours in some cases. For precautionary reasons, the practitioner may start at the preferred working dosage level of 0.1 ml as described above, or perhaps at a reduced level, say 0.05 ml, and then observe if a delayed hypersensitive reaction results. If after a reasonable interval, no such reaction occurs, then a further dose at an increased level can be administered and so on until the threshold for delayed hypersensitivity has been reached. In patients suffering a severe onslaught of the disease or in a considerably debilitated state due to a chronically persisting disease, who are deemed for present purposes to be in a seriously immuno-deficient state, larger dosage levels may be required to achieve a delayed hypersensitivity. If delayed hypersensitivity does not appear after several injections with working dosages ranging as high as 0.3 ml, then the conclusion follows that the immunodefense system of that patient has become so weakened as to be beyond recovery and the prognosis for such a patient must be taken as extremely poor. A total dosage as high as about 0.5 ml is presently considered as approaching destructive levels and should be avoided.

DESCRIPTION OF CONSTITUENT VACCINES

A preferred rabies vaccine is a suckling mouse brain vaccine (SMBV) obtained from Sanidad Publica, Guatamala, but in principle any rabies vaccine which is deemed safe for administration to human beings is presumed to be effective as the rabies vaccine component of the present invention. As is known, before the last thirty years, rabies vaccines were derived from the brain tissue of mammals having a mature central nervous system, the virus in such preparations being partially or completely inactivated so as to reduce the risk of uncontrolled infection upon administration to humans. Vaccines of this type containing residual live virus have been proscribed from use for humans by the World Health Organization because their use in man is associated with a significant risk of post-vaccinal reactions and paralytic accidents from an encephalitogen in mature brain tissue, and consequently should be avoided if at all possible in the preparation of the instant composite vaccine except in circumstances where such a vaccine is the only material which is available under particular local circumstances. The so-called Fermi rabies vaccine within this category must still be in use in certain countries and may be used as a last resort if no alternative is available.

A preferred rabies vaccine is derived from the brain tissue of very young animals with an immature central nervous system where the virus content has been inactivated in various ways, a preferred type being the so-called suckling mouse brain vaccine mentioned above although similar vaccines can be obtained from suckling rat brains and suckling rabbit brains. The risk of a paralytic reaction to such vaccines is much reduced. In addition, other rabies vaccines are prepared by growing the virus in chicken or duck embryos (DEV) with repeated passages through numbers of eggs so as to reduce the activity of the virus. Both so-called high and low passage vaccines are available and are typically utilized for the innoculation of pets both canine and feline as well as cattle. More preferable for humans are avian embryo vaccines inactivated, for example, by treatment with BPL, and a duck embryo vaccine obtained in this fashion is widely regarded as safe for administration to humans and can be incorporated in the present composite vaccine. A recent development is the human diploid cell vaccine (HDCV) which is considered effective and safe and can be employed here.

As noted above, a rabies vaccine is typically administered in a post-exposure treatment for rabies, which is its usual modality, pre-exposure immunization being applied only to persons in an environment presenting an extraordinarily high risk of exposure, at levels of about 2 ml. In the present invention, the amount of the rabies vaccine is present in a "nominal dose" of the composite vaccine at a considerably reduced level from a normal immunization dose. A rabies vaccine is generally considered as having strong antigenic potency, but its immunological reaction is rather specific to rabies virus although cross-reactions are quite possible, and consequently, the quantity of rabies vaccine in the inventive composite vaccine does not appear to be critical. Thus, as already suggested, the content of the rabies vaccine in a "nominal dose" can be increased within fairly broad limits without introducing risk of adverse consequences beyond the unavoidable slight risk to those few acutely hypersensitive individuals.

Incidentally, the so-called equine serum (ARS) administered in earlier times following possible exposure to rabies does not fall within the scope of the present invention because it is a serum containing antibodies from an external source and not a rabies antigen as such.

The preferred snake venom vaccine is that available under the trade name "Proven" from the Miami Serpentarium, Miami, Fla., which is believed to be within the scope of the Haast patent identified above, being obtained as a trivalent venom vaccine prepared according to the detailed description given in that patent, especially at column 11, line 22 et seq. Although, as the patentee recognizes, the viper component of that vaccine is primarily responsible for the immuno-stimulating action of the trivalent formulation and could, therefore, be employed in the present composite vaccine as the snake venom constituent thereof, it is believed more advantageous to include the entire trivalent preparation because the other venom components thereof, derived from a cobra venom and from a krait venom, respectively, appear to provide some immuno-stimulating action, notwithstanding that their primary effect is as neurotoxins.

While the "Proven" venom is particularly preferred, other snake venoms capable of creating an immunological response can certainly be substituted therefor, provided, of course, that the venom in question has been suitably detoxified and rendered reasonably safe for administration to humans. In this connection, Haast distinguishes between detoxification by selected chemical reactions such as oxidation and detoxification by purification routes designed to extract the noxious protein constituents of the venom. For present purposes, the term "detoxified" is used with more generalized significance to denote any snake venom which has been rendered essentially safe for injection in humans irrespective of the particular manner in which the venom has been processed to achieve such detoxification inasmuch as various routes to this end can be followed.

Alternative snake venom components are those described in U.S. Pat. No. 3,888,977 to Sanders et al and available from Sanders Medical Research Foundation, Boca Raton, Fla. These venoms are so-called modified snake venom neurotoxins which were developed especially for the treatment of neurological disorders such as amyotropic lateral sclerosis, multiple sclerosis and the like. The product of this patent is a venom from a snake species of the Bungarus genus or a mixture of such a venom with a venom component from a species of the Naja genus. In either case, the products are subjected to rather complex detoxification procedures as the patent disclosure sets forth.

In the context of the present composite vaccine, the snake venom constituent is mainly an adjuvant for enhancing the antigenicity of the other vaccine constituents due to its very powerful autogenic capacity.

The PPD vaccine is a tuberculin vaccine containing a purified protein derivative of the tuberculin bacillus such as is commonly employed in testing for the presence of antibodies against tubercle bacilli. A preferred PPD vaccine is that obtained from Japan BCG Laboratory, Tokyo, Japan. Before the availability of the PPD vaccine, the so-called Old Tuberculin vaccine served the same purpose, and while PPD is preferred, this substitution is possible if necessary. As a possible but less desirable alternative is a BCG vaccine, i.e., bacille Calmette Guerin vaccine, which contains living avirulent bovine-strain tubercle bacilli of the strain *Mycobacterium bovis.* The BCG vaccine is typically administered to provide a measure of protection against exposure to tuberculosis particularly to those in high risk situations rather than for diagnostic purposes and is more prone to be accompanied by undesirable side effects, particularly necrosis or ulceration at the injection site, and are for such reasons substituted only when unavoidable due to local circumstances.

The above described three constituent vaccines are considered essential to the composite vaccine of the present invention but are advantageously for maximum effectiveness supplemented by other constituent vaccines. The first choice of these other constituent vaccines is a DPT vaccine such as is available from the Swiss Institute of Serum Therapy and Vaccination of Bern, Switzerland. The DPT vaccine is a combined vaccine for diphtheria, pertussis (whooping cough) and tetanus that is commonly used for immunization of infants and preschool age children, and occasionally older children and adults, against these three infections. If the complete DPT vaccine is not available, a tetanus diphtheria toxoid adult type can be substituted or a diphtheria toxoid alone or a *Bordella pertussis* vaccine alone, all of which are available, or these individual vaccines can be combined to create essentially substantially the effect of the composite vaccine. Although the DPT vaccine is, strictly speaking, a trivalent vaccine in its own right, it is for purposes of analysis of the instant polyvalent vaccine treated as a single component.

A preferred mumps virus vaccine is that available from Eli Lily & Co., but other similar vaccines can be substituted. Such vaccines are generally prepared from embryonated egg tissues infected with mumps virus.

Dermatophytin is an extract of broth cultures of fungi causing ringworm and like mycotic skin infections, specifically *Trichophyton mentagraphytes, T. rubrum* and *T. Tonsurans,* available from the Hollister-Stier Division of Cutter Laboratories, Inc. of Berkley, Calif., as a desensitizing agent for the skin against such infections. The product is available at different dilution levels, specifically undiluted and at a 1:30 dilution ratio. In the ranges for the "nominal" dosages defined above, this component is employed at a dilution ratio of 1:100, but other dilution levels could be selected instead with corresponding adjustment in the amounts employed.

An alternative to the Dermatoophytin component is Dermatophytin "O" (Oidiomycin) which is a similar extract of a broth culture *Candida albicans,* which can also be involved in the etiology of ringworm and such yeast type infections as thrush in infants.

These Dermatophytin preparations are also commonly useful for skin test purposes, i.e., to determine by injection the development or not of a delayed hypersensitivity to either of the Tricophyton or Candida microorganisms, and similar skin test antigens for Candida, known as Candidins, can be an acceptable substitute.

In essence, the present invention amounts to the combination together into a single preparation of at least the first three of the above-named constituent vaccines and preferably the fourth and most preferably all six so as to create a new polyvalent composite vaccine which is administered in a single injection, in contravention of the normal strictures in medical circles against the simultaneous injection of separate different antigenic vaccines (exclusive of the DPT or the diphtheria tetanus toxoid vaccines which are universally accepted). By virtue of this combination, a large diversity of antigenic substances carrying multiple antigenic determinants are simultaneously introduced systemically to the patent so as to create a powerful stimulation to the immunological system, in order to produce a positive inhibition of the evolution of disease or a symptomatic relief and with respect to diseases that have no recognized relationship with the disease normally treated by each of the particular component vaccines in question. Thus, it appears that a distinct synergistic cooperation or action exists between the component vaccines identified above whereby when utilized in combination, an overall effect is achieved that substantially exceeds what would be expected from their behavior separately.

The amounts of the individual constituent vaccines specified above are based on experiments with the particular vaccine preparations identified in the preceding description; and if other vaccine preparations of commerce are substituted, these proportions may require adjustment to account for possible differences in potency between the preparations in question. More specifically, there will exist for each such commercial preparation a recommended dosage level for its usual intended purpose, and by comparing these recommended dosage levels, the practitioner can make a determination of their relative potencies which can serve as a guide for making the necessary change in the dosage levels to maintain a generally fixed antigenic activity for that constituent vaccine within the overall composite vaccine. For example, if a HDCV rabies vaccine were to be substituted for an SMBV vaccine and the recommended dosage of the former were twice that of the latter as a preventative for rabies, then the quantity of the HDCV here would likewise be doubled.

It will be appreciated that, inasmuch as the instant polyvalent vaccine utilizes constituent vaccines which have been commercially available and in use in their own right for lengthy periods of time, the present vaccine is free of the usual problems and complications involved in achieving the practical manufacture as well as the approval of the medical community for newly developed vaccines. That is to say, since the individual constituent vaccines are accepted for safe administration to humans, within the recognized constraints for safe use inherent in any injected vaccine, the combination of these individually safe materials at much reduced levels is consequently prima facie safe for administration to humans within these same constraints.

As presently understood, the instant vaccine should be administered by subcutaneous injection. It is known that some of the constituent vaccines may be accompanied by complications if injected through other routes and based on available information, other administration modes are contraindicated.

The polyvalent vaccine compositions of the present invention have been used for the treatment of a number of patients suffering from a considerable variety of diseases, particularly of viral or autoimmune origin, according to the following general summary. (1) Viral disorders grouped under the general heading of neuralgia or neuritis including acute facial paralysis, trigeminal neuralgia, sciatic neuritis, intercostal neuritis, spermatic cord pain, and neuritis of the abdominal nerves, for which the instant vaccine proved a highly effective treatment using, for example, in the case of trigeminal neuralgia a minimum of 4 doses, a maximum of 8 doses and a mean of 6.25 dosages covering a treatment period of 8 to 16 days with a mean duration of 10.25 days. (2) The herpes complex including *Herpes Zoster* and *Herpes labialis* and *genitalis* which were treated effectively and rapidly in quite constant and definite fashion by the present vaccine with the avoidance of secuelae including the post-herpetic neuralgia, using a minimum of 2 to a maximum of 10 dosages with a mean of 5.5 dosages for *Herpes Zoster* with a variety of different nerve involvements; and *Herpes genitalis* using a range of 3–6 dosages over a mean treatment period of 6 days with pain relief being achieved in most cases after only 2 doses. (3) Eruptive fevers in children especially measles which could be controlled by the instant vaccine, resulting in only a mild course of the disease, avoiding more serious consequences including complications and the considerable shortening of the course of the disease. For measles in the young up to early adulthood, 2–3 doses sufficed covering a treatment period of 2–4 days with a mean duration of 2.5 days. (4) Mumps (acute parotitis) wherein 2–4 doses greatly alleviated the severity of the disease and avoided acute discomfort and possible complications. (5) Psoriasis for which the present vaccine proved more beneficial than conventional treatment. (6) Arthritis and related collagen diseases, such as rheumatoid arthritis, osteoarthritis, sclerodermia and related autoimmune diseases which were mitigated by frequent periodic doses at the beginning and then at reduced frequency according to developments. (7) Multiple sclerosis where progression of disease was slowed and troublesome symptoms improved. (8) Viral hepatitis in which the duration of the disease was noticably shortened and complications reduced.

Included in the above general summary are diseases which are of recognized chronicity and in some cases are subject to spontaneous relapses and remissions in their natural progression. Further, due to unavoidable circumstances, it was impossible to maintain any long term surveillance over many of the patients who have been treated in accordance with this invention. For these reasons, it would be unrealistic to assert that the instant vaccine exerted total curative effects for such diseases; nevertheless significant symptomatic alleviation or relief coupled with perceptible mitigation of the immediate state of the disease could consistently and demonstrably be achieved upon administration of the instant polyvalent vaccine.

The following is a summary of the salient findings of a number of case histories demonstrating the effects of the instant vaccine, and in these case histories the abbreviations "Dx" and "Tx" signify the diagnosis and treatment, respectively. The designation (Q) signifies that a "quadravalent" combination consisting of the basic trivalent vaccine plus the DPT vaccine was administered; otherwise, the vaccine was the preferred hexavalent vaccine, all the constituent vaccines being present at the normal specified level as designated in the preferred formation above.

Description of Clinical Cases

Rheumatoid Arthritis and Related Collagen Diseases

Case 1: 66 year-old housewife. Over one year, arthritis involving joints of the feet, knees and hands, with no remissions. Dx: degenerative processes of the joints. Tx: "Polyvalent Vaccine" was applied daily for 1 week at 0.1 ml then 3 times weekly. Responded very favorably, can walk and use her hands more efficiently.

Case 2: 51 year-old housewife. Long period of arthritic pains over spine, elbows and joints in general. Tx: "Polyvalent Vaccine" was applied every two days and every three days for 3 weeks. Responded very rapidly. Edema disappeared. Can move around without pain and use her hands well.

Case 3: 61 year-old male. Whiplash from rear end collision 10 years ago. X-rays of Cervical Spine shows narrowing of C5, C6, C7 and T1 Spaces with osteophytic formation and partial narrowing of intervertabral foramina. Had retired. Tx: Started "Polyvalent Vaccine" treatment with 2 injections a week for 2 months and then one injection of 0.1 ml a week for another 3 months and then every fifteen days. Pain disappeared and was able to move his neck very well. Still under treatment after 2 years but thinking of going back to work.

Case 4: 48 year-old housewife. Pain in elbow and right hand of 4 months duration. Diabetic. Dorsal right pain. Osteoarthritis and diabetic neuritis. Tx: "Polyvalent Vaccine" was applied every 3 days 0.1 ml for 3 weeks. Excellent response.

Case 5: 59 year-old housewife. Rheumatoid arthritis for 5 years with pain and edema of the knees, shoulders, hands and neck. Tx: "Polyvalent Vaccine" applied every day for 4 weeks for one month. Patient feels better, can move around, more strength and edema has subsided partially. Treatment discontinued prematurely.

Case 6: 56 year-old male. Agriculture. Diabetic. Psoriasis. Dorsal and lumbar pain. Psoriatic arthritis. Tx: "Polyvalent Vaccine" was applied 0.1 ml three times a week for 3 months. Patient improved considerably, pain reduced almost completely, psoriatic lesions have practically disappeared.

Case 7: 45 years old. Single. Male Osteoarthritis of the writs, hands, fingers and legs. Tx: "Polyvalent Vaccine" at 3 day intervals for 3 weeks. Patient reports increased use of hands and reduction of pain of hands and legs.

Case 8: 20 years old. Male. Student. Single, Acute Rheumatic Arthritis. Migratory pains of different joints. Tx: "Polyvalent Vaccine" for a period of one week daily 0.1 ml. Patient was relieved but could not continue with treatment.

Case 9: 66 year-old housewife. Pain of the knees. Chest pain and poor ventilation, dispnea on exercise. Cough. Sclero-emphysema and osteo-arthritis. Tx: "Polyvalent Vaccine" every day for two months, then every fifteen days for next 4 months. Osteo-arthritic pains substantially better after 4th dose.

Case 10: 28 year-old female. Teacher and secretary. Pain in spine, pelvic region and joints of hips for 1 year. Rx: "Polyvalent Vaccine" applied 0.1 ml weekly for 3 months. Injections were discontinued because of relief of pain and stabilization.

Case 11: 35 year-old housewife. Joint pains of legs and spine, unable to sit up and limitation to walk because of exacerbation of pain, predominantly in knees and ankles Tx: 0.1 ml of "Polyvalent Vaccine" every other day; 5 doses in 10 days. Patient relieved of pain, but will come back for further treatment.

Case 12: 77 years. Female. Rheumatoid osteoarthritis for 5 years. Symmetrically in both wrists, elboes and ankles. Tx: "Polyvalent Vaccine" 0.1 ml 3 times weekly for 2 weeks, then twice weekly for 4 weeks. Continuing one dose a week indefinitely. Relief was great; pain disappeared with 3rd dose.

Case 13: 39 year-old married housewife with 3 children. Started 2 years ago with slight pain in wrist joints. Was infiltrated with dexamethasone and relieved of pain. 6 months later she was told she had high uric acid, because her pains recurred. Treated with Zyloprim with no relief, then Motrin, Clinoril, Naprosine, Indocid because of arthritic pains of her wrists, shoulders, neck, spine, feet and ankles. Tx: treatment started with "Polyvalent Vaccine" and continued for 12 months. For the first 3 weeks every day 0.1 s.c. then 3 times weekly for 2 months and now twice a week. She cannot do without the vaccine for more than 1 week.

Sjogren's Syndrome

Case 14: Female. 49 years old. Married. 5 children. When 18 years joint pains and skin rash diagnosed as Rheumatic Fever. Treated with Penicillin L.A. until sensitivity developed, then anti-histaminic drug. Later, dryness of the skin (Xeroderma) scaling, allergic rhinitis, dryness of the nasal mucosa and involvement of respiratory tract with production of thick tenacious sputum. Articular lesions progressed. Had replacement of hip joint, replacement of wrist and extensor tendon of 5th finger, left. Keratoconjunctivitis sicca and small tumors under the skin. Limited flexion and extension of fingers and wrist joints predominantly right side. Loss of strength in most systemic muscles. Osteophytes of the left foot with fusion of astragalus and calcaneus. Hematurias periodically. Prior Tx: Aralen, Prednisone, Motrin, Naprosine, Nalfon, Feldene Clynoryl, besides Sintroid for Hypothyroidism. Vitamins B12 and A. Natural Tears, etc. Tx: "Polyvalent Vaccine" 0.1 ml every other day for two weeks. Improvement almost immediately in joint pains, dryness of skin and bronchial secretions, etc. Polyuria and edema is improving. Edema (due to cortisone) is improving.

Herpes Zoster

Case 15: Post-operative to brain surgery, 15 year-old girl developed Herpes Zoster involving eyes with severe swelling of lids. Two "Polyvalent Vaccine" (Q) doses of 0.1 were given on alternate days. Immediate improvement—lid-swelling gone.

Case 16: Female, 17 years, developed painful Herpes Zoster of abdomen. Tx: Five doses of "Polyvalent Vaccine" (Q) 0.1 ml on alternate days. Relief of pain on 2nd dose.

Case 17: Young male, 22 years. Herpes Zoster of ant. and post. neck and shoulder of five days duration. Tx:

Treated daily with 0.1 ml "Polyvalent Vaccine" (Q) for 5 days. Obtained relief after 2nd dose.

Case 18: 42 year-old female, married. Intercostal nerve Herpes Zoster of 24 days duration. Tx: Treated with "Polyvalent Vaccine" (Q) on alternate days with 9 doses of 0.1 ml. Lesions much improved.

Case 19: 45 year-old male. Severe Herpes Zoster of 2 days duration, left upper anterior chest and upper ant. arm, left post. neck. Tx: "Polyvalent Vaccine" (Q) every other day for 9 doses of 0.1 ml. Lesions almost completely healed.

Case 20: 15 year-old male. Herpetic lesions (Virus I) in lower lip and left lower lumbar region. Tx: 0.1 ml "Polyvalent Vaccine" (Q) every other day for 6 doses. Lip healed; back much improved.

Case 21: Female 36 years. Herpes Zoster appeared 3 days ago, intercostal nerve region. Tx: 0.1 ml dose "Polyvalent Vaccine" on alternate days. Five doses were needed for rapid response.

Case 22: Male 71 years, initiated Herpes Zoster 12 days before on the left forehead, eyelids, eye and nose. Excruciating pains. Tx: Treated on alternate days "Polyvalent Vaccine" (Q). 10 doses of 0.1 ml. Pain relieved and healing in progress.

Case 23: 57 year-old housewife. Intergluteal burning sensation, redness and swelling of 5 days duration. Intermittent pain irradiated to the pelvic region with sensation of pressure. Dx: Herpes Zoster. Tx: "Polyvalent Vaccine" applied 0.1 ml every day for 3 days and then alternate days for 3 doses. Pain relieved with third dose, lesion visibly healing.

Case 24: Female, 23 years. Housemaid. Single. Small vesicles face and neck 17 days duration. Itching and very painful. Dx: Herpes Zoster. Tx: "Polyvalent Vaccine" was administered 0.1 ml every other day for three days. Lesions virtually gone.

Severe Sepsis

Case 25: 49 year-old married housewife. Previous Dx: Cerebral vascular accident causing a paretic right upper and lower limb and inability to walk without help, but recovered with physiotherapy. Then started suffering with an universal headache, lack of sphincter controls and disorientation that evolved to coma. T.A.C. showed a left parasagital tumor that was excised through a left Temporoparietal Craniectomy. Pathology reported a meningioma. EEG showed Hydrocephalia that was treated with steroids and a Ventricularperitoneal derivation with a Denver valve was made. Developed a diffuse pneumonic infiltrate in both lungs. Treated with antibiotics, Methycillin, Gentamycin and Epamin. Needle aspiration of the brain recovered 3 ml of a pus-like material. Pateint severely ill, comatose and non-responsive to pain stimulus; death apparently imminent. Was presenting a necrotizing Herpes labialis I that invades both lips, tongue, larynx, cheeks. Is tachycardic, numerous mucous rales and very wet lungs. Tx: Started with "Polyvalent Vaccine" every day 0.1 ml as a last resort. Surprisingly, previous low-grade fever started peaking, patient started recovering consciousness after third dose. After seventh dose, she appears well oriented, responds well and the lesions on her lips, tongue, larynx and trachea are healing. The brain abscess was drained and edema has disappeared.

Herpes Labialis and Genitalis

Case 26: Female, 16 years old. Student, Single. Redness, erosion and swelling of the left third of the upper and lower lip, also a scabby small lesion on the right lower lip. Dx: *Herpes labialis*. Tx: 0.1 ml of "Polyvalent Vaccine" was applied. Second dose scheduled for 3rd day was unnecessary; lesions had already healed.

Case 27: Housewife, 23 years old. Ulceration from blister on midline of the lower lip with pain and itching. Tx: Dose with 0.1 ml of "Polyvalent Vaccine"; a day later second and final dose. Three days later she was healed.

Case 28: 4 year-old female with Herpetic lesions on lower lip, tip of the tongue and oro-pharynx, of 4 days duration. Tx: One dose of 0.05 ml "Polyvalent Vaccine". Failed to appear for next dose scheduled for next day. Four days later had healed.

Case 29: 21 year-old male. *Herpes Genitalis* of 15 days duration, penis red and ulcerated. Tx: "Polyvalent Vaccine" (Q) 0.1 ml given every other day for five doses. Appearance normal.

Case 30: 28 year-old male. *Herpes Genitalis* of 12 days duration. Previous attacks treated with Isoprinosine with healing always within 2 to 3 weeks. Tx: "Polyvalent Vaccine" every day for 4 doses. Healed in six days.

Case 31: 26 year-old male. *Herpes Genitalis* of one week duration. Tx: Only one dose of 0.1 "Polyvalent Vaccine". Healed in almost 4 days.

Case 32: 26 year-old female. *Herpes Genitalis*. Lesion on buttocks with excruciating pain irradiating to buttocks and legs. Tx: Two 0.1 ml doses "Polyvalent Vaccine" (Q) given every other day brought complete healing of lesion.

Case 33: 23 year-old female. *Herpes Genitalis* of 17 days duration. On left buttock with sciatic pain irradiation. Tx: 4 doses of "Polyvalent Vaccine" (Q) of 0.1 ml every other day. Healing almost complete.

Measles

Case 34: 12 year-old male. Student. Sick 8 days with eruptive fever Measles. Eruption has disappeared, but feels weak and astenic, has tenacious cough and diarrhea. Tx: "Polyvalent Vaccine" 0.05 ml every day for two days. Responded after the 1st dose. Astenia and soft stools disappeared. Cough gone after three days.

Case 35: 23-year old female. Had been breast feeding her child with Measles. Dx: Severe case of measles contracted from baby with probability of complications. Tx: "Polyvalent Vaccine" given 0.1 ml daily for three days. Eruption practically disappeared by 2nd dose; conjunctivitis and cough at 3rd dose.

Case 36: 48 year-old housewife. 12 days before had visitor with severe measles eruption and fever. 5 days later underwent a total abdominal Hysterectomy. 4 days later developed a severe pain in the legs, arms and abdomen and very high fever. Next day enanthema and exanthema appeared starting on face and thorax. Dx: Measles. Tx: 0.1 ml of "Polyvalent Vaccine" and repeated on next day. Eruption disappeared a day later and pain subsided within next two days.

Trigeminal Neuralgia (Tic douloureux)

Case 37: Housewife on tranquilizers for one year because of parasthetic sensations over right eye. Severe pain of the right mid-face for three months. No relief from analgesics. Tx: "Polyvalent Vaccine" (Q) 0.1 ml every other day for four doses. Complete relief after fourth dose.

Case 38: Housewife. Severe pain of her right midface four days ago. Dx: Trigeminal Neuralgia. Pain distributed in three divisions of the Trigeminal Nerve. Tx: "Polyvalent Vaccine" (Q) 0.1 ml every other day for five doses. Complete relief was obtained after 5th dose.

Case 39: Female, 23 years old. Pain in the forehead, temporal region and right cheek of 8 days duration. Has been treated with Tegretol, Vitamins B12, B1, B6. Had Facial Paralysis on same side earlier of 3 months duration. Secuelae of the facial paralysis are still present, slight assymmetry of face, etc. Tx: "Polyvalent Vaccine" (Q) 0.1 ml every other day for 5 doses. Recovered completely.

Acute Facial Paralysis

Case 40: Male. 24 years. Cook. After cold night at work, noticed that features were deviated to left, could not eat well and could not close right eye. Dx: Facial paralysis of the right side. Tx: "Polyvalent Vaccine" every day for 4 days at 0.1 ml. Then every other day for five more doses. A diuretic and an anti-inflammatory were added to treatment. Patient first recovered movement of right eyelid, then movement of facial muscles.

Case 41: Female. Single. Student, 17 years old. After final tests of the year, and very hard studying for a few days and nights, suffered from left Facial Paralysis and Mastoid pain on left side. Tx: "Polyvalent Vaccine" every day 0.1 ml for 4 days and then every other day for 2 more doses. A diuretic and an anti-inflammatory drug were used at the same time. Patient recovered movements of face.

Case 42: Housewife. Diabetic under control Left Facial Paralysis and slight fever of one month duration. Tx: 0.1 ml of "Polyvalent Vaccine" every other day for 8 doses before starting to recover movement of eyelids. After 13th dose she was almost well, although left side of the face gets tired very often and shows signs of paretic trouble.

Case 43: 10 year-old male. Student. Right Facial Paralysis dating 8 weeks. Treated elsewhere with the conventional procedures, Phisiotherapy and Vitamin B1, B6, B12, to no avail. Has suffered from the Grippe repeatedly. Tx: "Polyvalent Vaccine" every other day 0.1 ml for 20 doses. Has had partial recovery.

Case 44: Female, 14 years. Facial Paralysis of one week's duration. Not able to close her eyelids on the right side and had epiphora. Left corner of mouth deviated and would dribble when eating. Tx: 0.1 ml "Polyvalent Vaccine" (Q) every day for 4 doses and then every other day for 2 doses. Can now close eye; while smiling still a small deviation of mouth. Two more doses of vaccine recommended.

Mumps (Acute parotitis)

Case 45: 13 year-old male. Suffering from a swollen neck, swollen salivary glands, red edematous orifices of Stenson's ducts. Developed left orchitis with another elevation of fever and tenderness and swelling of left testicle. Dx: Epidemic Parotitis complicated with acute infectious orchitis. Tx: 0.1 ml "Polyvalent Vaccine" for 2 days. Swelling and tenderness subsided on third day, transforming a severe case into a slight one, relieving patient of gonadal discomfort and swelling.

Case 46: 16 year-old female, student. Swollen right parotid gland, lifting the lobule of the ear. Tender on palpation, discolored and with red edematous orifice of the right Stenson's duct. Slight fever of 101°, headache and lack of appetite. Tx: Sent to bed and started on "Polyvalent Vaccine" 0.1 ml every day for three days. Swelling disappeared and all other symptoms subsided; patient felt well at this time.

Case 47: 36 year-old female. Swelling on left side of face. Noted slight paralysis on left side of mouth and unable to comfortably shut left eyelids completely. Swollen mass coincides with the parotid gland that was tender on palpation and Stenson's left orifice was red and edematous. Slight fever and headache. Tx: 0.1 ml of "Polyvalent Vaccine" daily for 4 doses. Swelling subsided after fourth dose.

Laryngeal Papillomatosis

Case 48: Male. 10 years. Student. Suffering for six years from Juvenile Laryngeal Papillomatosis. Has undergone excision under general anesthesia through endoscopy 15 times for papillomas of the vocal chords and larynx. Sometimes dyspneic and easily tired by light exercise. Disphonia present. Tx: "Polyvalent Vaccine" (Q) 0.1 ml every day for 2 weeks and then every other day for 8 weeks. Then irregularly for 4 months. While on vaccine underwent a control procedure with general anesthesia and microlaringoscopy. Endoscopist reported that papillomatous vegetations were very soft, very small and easily resectable. No recurrence after 7th month of treatment. Voice is normal and can exercise freely.

Case 49: 31 year-old housewife. Had undergone 121 resections for papillomas of the vocal chords and larynx, recurring about every 6–8 weeks. Tx: 0.1 ml of "Polyvalent Vaccine" (Q) every other day for 4 months. No further endoscopic procedures and excisions needed.

Multiple Sclerosis

Case 50: 32 year-old housewife. Started four years ago with paresthetic sensations consisting of tingling and numbness on the outside of both thighs, left hand, thumb and fifth finger also lack of sensitivity. Pain under her left breast. Blurred vision of the right eye. Dx: Multiple Sclerosis. Tx: "Polyvalent Vaccine" (Q) 0.1 ml daily for 3 days, then three times a week and then twice a week indefinitely. Patient felt better, stopped paresthetic sensations, could use hands better and eyes stopped troubling her.

Case 51: Veterinarian, male. 44 years. Married. 10 years ago, started with weakness from the waist down. Unable to walk for one week—weakness and loss of control of both lower limbs. Then developed disarthria, double vision, hand tremor and weakness. Difficulty in starting micturition. Loss of memory. Tx: 0.1 ml "Polyvalent Vaccine" (Q) 3 times weekly for four months. Recovered vision, did not tire, could eat better, sleep better and had become better coordinated and improved balance. Unfortunately, treatment interrupted because of personal problems, losing benefits gained from treatment. Recently returned to Tx and is slowly regaining strength and vision.

Case 52: 64 year-old housewife. 3 years ago had lost complete control of her lower limbs; could not walk without assistance because of incoordination and weakness. Very difficult to understand speech, did not pronounce well. Severe dysarthria and she flings her upper and lower limbs when attempting volitional activity. Dx: Multiple Sclerosis. Tx: "Polyvalent Vaccine" (Q) 0.1 ml three times a week for 2 months and then twice a week indefinitely. When she is unable to receive her treatment she feels choking sensation.

Severe Acne

Case 53: 19 year-old student. For 6 years acne profusely on the thorax, neck, face and dorsum. No drugs have had any effect. The acne appears in various stages, from pustules to bleeding lesions, lesions with scabs, lesions that are healing, hypertrophic scars, etc. The lesions are so luxuriant that they are almost confluent. Tx: "Polyvalent Vaccine" 0.1 ml every day for 4 days and then three times weekly. Severity has subsided and treatment is continuing.

What is claimed is:

1. A non-specific therapeutic polyvalent vaccine for stimulating the immuno-defense system of a patient suffering from neuralgia, herpes complex, measles, mumps, psoriasis, arthritis, multiple sclerosis, viral hepatitis, and acne and providing symptomatic relief therefor, which consists essentially of a therapeutic amount of a mixture of a purified protein derivative (PDD) vaccine, a rabies vaccine, and snake venom vaccine.

2. A polyvalent vaccine of claim 1 containing in addition a combined diphtheria, tetanus, pertusis (DTP) vaccine as adjuvant.

3. A polyvalent vaccine of claim 2 containing in addition a mumps virus vaccine and Dermatophytin vaccine.

4. The polyvalent vaccine of claim 3 wherein said constituent vaccines are present in an individual dosage in the following ranges of proportions

| Constituent Vaccine | Minimum (ml) | Maximum (ml) |
|---|---|---|
| PPD Vaccine | 0.001 | 0.01 |
| Rabies Vaccine | 0.005 | 0.10 |
| Snake Venom Vaccine | 0.05 | 0.15 |
| DPT Vaccine | 0.001 | 0.01 |
| Mumps Vaccine | 0.001 | 0.01 |
| Dermatophytin Vaccine at 1:100 dilution | 0.001 | 0.01 |

5. A method for stimulating the immune defense system of a patient suffering from neuralgia, herpes complex, measles, mumps, psoriasis, arthritis, multiple sclerosis, viral hepatitis, and acne which comprises administering to the patient for introduction into the system thereof a disease mitigating amount of the polyvalent vaccine of claim 1.

6. A method for stimulating the immune defense system of a patient suffering from neuralgia, herpes complex, measles, mumps, psoriasis, arthritis, multiple sclerosis, viral hepatitis, and acne which comprises administering to the patient for introduction into the humoral system thereof a disease mitigating amount of the polyvalent viral vaccine of claim 2.

7. A method for stimulating the immune defense system of a patient suffering from neuralgia, herpes complex, measles, mumps, psoriasis, arthritis, multiple sclerosis, viral hepatitis, and acne which comprises administering to the patient for introduction into the humoral system thereof a disease mitigating amount of the polyvalent viral vaccine of claim 3.

8. The method of claim 1 wherein said vaccine is administered subcutaneously.

* * * * *